United States Patent [19]

Böhner

[11] Patent Number: 4,622,397
[45] Date of Patent: Nov. 11, 1986

[54] 3-CHLORO-AS-TRIAZIN-5-ONES

[75] Inventor: Beat Böhner, Binningen, Switzerland

[73] Assignee: Ciba-Geigy Corporation, Ardsley, N.Y.

[21] Appl. No.: 752,288

[22] Filed: Jul. 5, 1985

[30] Foreign Application Priority Data

Jul. 12, 1984 [CH] Switzerland ............ 3403/84

[51] Int. Cl.$^4$ ............................. C07D 253/06
[52] U.S. Cl. ..................... 544/182; 544/112; 71/93
[58] Field of Search ............ 71/93; 544/182, 112

[56] References Cited

U.S. PATENT DOCUMENTS 4,447,258 5/1984 Dickore et al. ............ 544/182

OTHER PUBLICATIONS

Dickore et al., Chemical Abstracts, vol. 94, entry 103438u (1981).
Timmler et al., Chemical Abstracts, vol. 71, entry 39014y (1969).

Primary Examiner—John M. Ford
Attorney, Agent, or Firm—Edward McC. Roberts; Kevin T. Mansfield

[57] ABSTRACT

The invention relates to a process for the preparation of aminotriazinone derivatives of the formula I

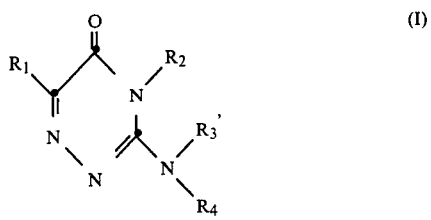

wherein $R_1$ and $R_2$ are each independently alkyl, cycloalkyl, aralkyl or aryl, and
$R_3$ and $R_4$ are each independently hydrogen, alkyl or cycloalkyl, or together with the nitrogen atom to which they are attached are a piperidine or morpholine ring, which process comprises phosgenating a compound of formula II

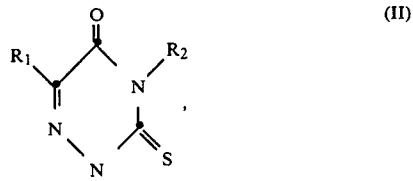

wherein $R_1$ and $R_2$ are as defined above, and reacting the resultant compound of formula III

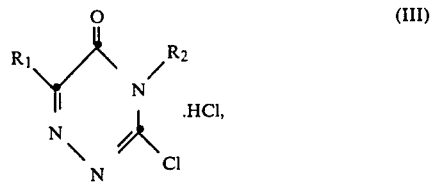

wherein $R_1$ and $R_2$ are as defined above, without isolation or after isolation, with a compound of formula IV

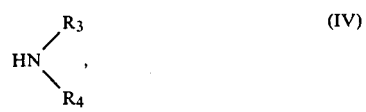

wherein $R_3$ and $R_4$ are as defined above.

The invention also relates to the novel compounds of formula I and to the use thereof for controlling undesirable plant growth, as well as to compounds of the formula III.

3 Claims, No Drawings

3-CHLORO-AS-TRIAZIN-5-ONES

The present invention relates to a novel process for the preparation of aminotriazinone derivatives, to the novel aminotriazinone derivatives themselves and to compositions containing them, and also relates to the use of these novel derivatives or compositions containing them for controlling undesirable plant growth. The invention further relates to novel intermediates developed for the process of this invention.

Some of the triazinone derivatives which can be prepared by the process of this invention are novel, and some are described in European patent publication No. 15 452 and U.S. Pat. No. 3 544 570, together with a process for their preparation. In one process disclosed in these publications, aminotriazinones are prepared by reacting a triazinone which carries a substituted mercapto group with an unsubstituted or substituted amino group or with an N-heterocycle. Further, the European patent publication referred to above describes a process for the preparation of aminotriazinone derivatives in which an α-ketonic acid is reacted with a 3-amino-1,1,2-trimethylguanidinium salt which has been obtained from a 1,1,2,3-tetramethylisothiuronium salt by reaction with hydrazine hydrate.

Thus in the known processes a substituted mercapto group, usually a methylmercapto group, is removed in the course of the synthesis, so giving rise to environmental problems. Moreover, as the methylmercapto group is only a moderately reactive leaving group, the reactions with amines often take place only at elevated temperature, so that yields are frequently poor or impure reaction products are obtained.

Hence it is an object of the present invention to provide a process that avoids the occurrence of environmentally harmful by-products and affords the aminotriazinone derivatives in good yield and in pure form.

Surprisingly, it has now been found that aminotriazinone derivatives can be prepared in another and environmentally more advantageous manner.

Accordingly, the present invention relates to a process for the preparation of aminotriazinone derivatives of the formula I

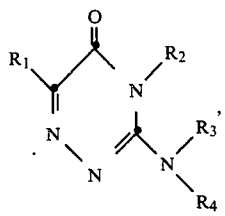

wherein
$R_1$ and $R_2$, each independently of the other, are alkyl which is unsubstituted or substituted by alkoxy or halogen; or cycloalkyl which is unsubstituted or substituted by methyl; aralkyl which is unsubstituted or substituted by one or more members selected from the group consisting of halogen, alkyl, haloalkyl and alkoxy; or are aryl which is unsubstituted or substituted by one or more members selected from the group consisting of alkyl, halogen, haloalkyl and alkoxy; and
$R_3$ and $R_4$, each independently of the other, are hydrogen, alkyl, cycloalkyl which is unsubstituted or substituted by methyl; or $R_3$ and $R_4$, together with the nitrogen atom to which they are attached, are a piperidine or morpholine ring, which process comprises phosgenating a compound of formula II

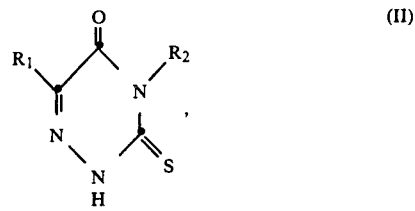

wherein $R_1$ and $R_2$ are as defined above, and reacting the compound of formula III so obtained

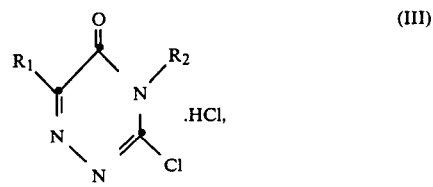

wherein $R_1$ and $R_2$ are as defined above, without isolation or after isolation, with a compound of formula IV

wherein $R_3$ and $R_4$ are as defined above.

Alkyl groups $R_1$, $R_2$, $R_3$ or $R_4$ present as substituents in the compounds of formula I, or as moiety of the substituents $R_1$ and $R_2$, may be straight chain or branched and contain as a rule 1 to 8, preferably 1 to 5, carbon atoms. Such groups comprise methyl, ethyl, n-propyl, isopropyl, n-butyl, isobutyl, sec-butyl and tert-butyl, as well as n-pentyl, n-hexyl, n-heptyl, n-octyl and their isomers.

Suitable alkoxy groups are preferably those containing 1 to 4 carbon atoms, i.e. methoxy, ethoxy, n-propoxy, isopropoxy, n-butoxy, isobutoxy, sec-butoxy and tert-butoxy.

Halogen as substituent or as moiety of a substituent is fluorine, chlorine, bromine and iodine, with fluorine and chlorine being preferred.

Haloalkyl groups normally contain 1 to 4, preferably 1 or 2, carbon atoms and may be mono- or perhalogenated. Preferably they contain 1 to 3 halogen atoms. Examples of haloalkyl groups are: 1,1,-dimethyl-2-chloroethyl, 1-methyl-3-fluoropropyl, trichloromethyl, 3,3,3-trifluoropropyl, 2,3-dichloro-2-methylpropyl, 1-(chloromethyl)ethyl, trifluoromethyl, 1-(fluoromethyl)ethyl, 1,1-dimethyl-3-chloropropyl, 1-methyl-3-chloropropyl and 1,1-dimethyl-2-fluoroethyl.

Aryl groups contain as a rule 6 to 18 carbon atoms. Phenyl and naphthyl are preferred.

Aralkyl groups are preferably those containing 6 to 10 carbon atoms in the aromatic moiety and 1 to 4 carbon atoms in the alkyl moiety. Benzyl is preferred.

Aryl as substituent or moiety of a substituent may be substituted by members selected from the group consisting of halogen, alkyl, haloalkyl and alkoxy, preferably by 1 to 3 such substituents.

Examples of substituted aryl groups are: 2-methoxy-4-chlorophenyl, 3-chloro-4-trifluoromethylphenyl, 2,6-dimethoxyphenyl, 2,4,6-trifluorophenyl, 2-chloro-4-ethoxyphenyl, 2,4-dimethoxyphenyl, 2-chloro-4-trifluoromethylphenyl, 2,4-difluorophenyl, 4-chloromethylphenyl, 3-dichloromethylphenyl, 2-chloro-4-methoxyphenyl, 4-methoxy-α-naphthyl, 6,7-dichloro-α-naphthyl and 3-chloromethyl-β-naphthyl. Examples of substituted aralkyl groups are: 2-(2-chloro-4-trifluoromethylphenyl)ethyl, 4-methoxybenzyl, 2,4,6-trifluorobenzyl, 2-(2,4-dimethoxyphenyl)ethyl, 2-chloro-4-trifluoromethylbenzyl, 3,5-dichlorobenzyl and 4-trifluoromethylbenzyl.

Cycloalkyl is cyclopropyl, cyclobutyl, cyclopentyl, cyclohexyl, cycloheptyl and cyclooctyl. The cycloalkyl groups are unsubstituted or methyl-substituted. The cycloalkyl groups preferably contain 1 or 2 methyl groups.

The phosgenation of a compound of formula II, which may also be in tautomeric form as

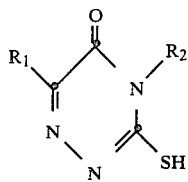

is conveniently carried out in a solvent or diluent which is inert to phosgene, in the temperature range from 0° to 80° C., preferably from 20° to 50° C., and under normal pressure.

In general, it is possible to effect complete reaction by stirring the reaction mixture for 14 to 16 hours in the temperature range from about 20° to 25° C., or for 1 to 2 hours at about 45° C.

Suitable solvents are in particular aromatic and aliphatic hydrocarbons, for example benzene and toluene; halogenated hydrocarbons such as chloroform amd carbon tetrachloride; and esters of organic acids such as ethyl acetate.

It is particularly advantageous to use a solvent in which the hydrochloride of the 3-chlorotriazinones of formula III are sparingly soluble, as these compounds may thus be readily isolated by filtration.

In the phosgenation of compounds of formula II, the resultant 3-chlorotriazinones are obtained in the form of hydrochlorides and can be reacted as such. The free form of the 3-chlorotriazinones can be prepared very readily by sublimation, for example in a high vacuum.

The compounds of formula III in the form of their hydrochlorides and in the free form are novel intermediates developed for the process of this invention and thus constitute an object of the invention.

Particularly interesting 3-chlorotriazinones are those of formula III, wherein $R_1$ is sec-butyl, 1-ethyl-n-propyl or, preferably, cyclohexyl, tert-butyl or isopropyl, and $R_2$ is methyl.

The reaction of a compound of formula III in the form of its hydrochloride, or as free compound, with a compound of formula IV is conveniently carried out in an inert solvent or diluent and in the presence of a base, and in the temperature range from 0° to 150° C., preferably from 20° to 80° C.

Particularly suitable solvents are aliphatic and aromatic hydrocarbons, for example benzene, toluene, xylenes, petroleum ether, cyclohexane, n-hexane; halogenated hydrocarbons such as chlorobenzene, methylene chloride, ethylene chloride, chloroform, carbon tetrachloride, tetrachloroethylene; ethers and ethereal compounds, for example dialkyl ethers such as diethyl ether and diisopropyl ether; or mixtures of such solvents with one another.

Suitable bases are in general inorganic bases selected from the series consisting of: hydrides, for example sodium hydride or calcium hydride; oxides, for example magnesium oxide, calcium oxide or sodium oxide; hydroxides, for example lithium hydroxide, sodium hydroxide or potassium hydroxide; or carbonates, for example sodium carbonate or potassium carbonate; or organic bases such as triethylamine, trimethylamine, pyridine, or an excess of the amine of formula IV.

The starting materials of formulae II and IV are known or they can be obtained by methods analogous to known ones.

Novel aminotriazinone derivatives of formula I constitute a further object of the invention. Novel aminotriazinones moiting particular interest are those of formula Ia falling under the scope of formula I

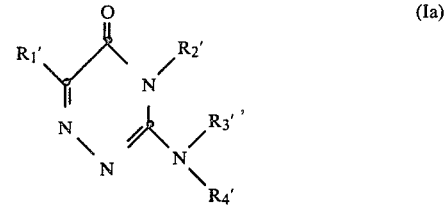

wherein $R_1'$ is isopropyl, sec-butyl, tert-butyl, 1-ethyl-n-propyl or cyclohexyl, $R_2'$ is methyl, and $R_3'$ is hydrogen and $R_4'$ is methyl or ethyl, or $R_3'$ and $R_4'$ are each methyl, with the proviso that (i) $R_3'$ is hydrogen if $R_1'$ is sec-butyl, tert-butyl, 1-ethyl-n-propyl or cyclohexyl, and (ii) $R_3'$ is methyl if $R_1'$ is isopropyl; and are preferably 3-ethylamino-6-cyclohexyl-4-methyl-1,2,4-triazin-5-one, 6-(1-ethyl-n-propyl)-4-methyl-3-methylamino-1,2,4-triazin-5-one, 6-sec-butyl-4-methyl-3-methylamino-1,2,4-triazin-5-one and, most preferably, 6-cyclohexyl-4-methyl-3-methylamino-1,2,4-triazin-5-one, 6-tert-butyl-4-methyl-3-methylamino-1,2,4-triazin-5-one and 3-dimethylamino-6-isopropyl-4-methyl-1,2,4-triazin-5-one.

The compounds of formula Ia have pronounced herbicidal activity. To be singled out for special mention on account of their outstanding activity are: 6-cyclohexyl-4-methyl-3-methylamino-1,2,4-triazin-5(4H)-one, 6-tert-butyl-4-methyl-3-methylamino-1,2,4-triazin-5(4H)-one and, most preferably, 3-dimethylamino-6-isopropyl-4-methyl-1,2,4-triazin-5(4H)-one.

For application as herbicides, the compounds of formula Ia are used in unmodified form or, preferably, together with the adjuvants conventionally employed in the art of formulation, and are therefore formulated in known manner e.g. to emulsifiable concentrates, coatable pastes, directly sprayable or dilutable solutions, dilute emulsions, wettable powders, soluble powders, dusts, granulates, and also encapsulations in e.g.

polymeric substances. As with the nature of the compositions, the methods of application, such as spraying, atomising, dusting, scattering, coating or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils, for example epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$ alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensation product of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$ alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1980; Helmut Stache, "Tensid-Taschenbuch" (Handbook of Surfactants), Carl Hanser Verlag, Munich/Vienna, 1981.

The agrochemical compositions usually contain 0.1 to 99%, preferably 0.1 to 95%, of a compound of the formula I, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients such as stabilisers, antifoams, viscosity regulators, binders, tackifiers as well as fertilisers or other active ingredients for obtaining special effects.

Aminotriazinone-derivatives of formula Ia, in particular 3-dimethylamino-6-isopropyl-4-methyl-1,2,4-triazin-5(4H)-one, are preeminently suitable for controlling monocot and dicot weeds, both by preemergence and postemergence treatment.

The aminotriazinone derivatives of formula Ia, or compositions containing them, can be used with particular advantage for selectively controlling weeds in crops of useful plants, for example in crops of cereals, soybeans, potatoes, tomatoes and sugar cane.

7

The rates of application in which the compounds are employed depend on the respective conditions, for example in particular the weather conditions, the nature of the soil, the plant growth and the time of application. In general, rates of application of 30 to 2000 g, in particular of 100 to 500 g, of active ingredient per hectare have proved advantageous.

EXAMPLE 1

Preparation of
3-chloro-6-isopropyl-4-methyl-1,2,4-triazin-5(4H)-one hydrochloride To a solution of 34.6 g (0.35 mole) of phosgene in 600 ml of acetic acid are added 60 g (0.35 mole) of 6-isopropyl-4-methyl-3-mercapto-1,2,4-triazin-5(4H)-one. After the slightly exothermic reaction has subsided, the reaction mixture is stirred for 1 hour at 25° C. The precipitate is isolated by filtration and washed with a small amount of ethyl acetate, affording 64.5 g (90% of theory) of 3-chloro-6-isopropyl-4-methyl-1,2,4-triazin-5(4H)-one hydrochloride with a melting point of 120° C. (dec.).

Subsequent sublimation of the above product in a high vacuum affards the free 3-chloro-6-isopropyl-4-methyl-1,2,4-triazin-5(4H)-one with a melting point of 144° C. (dec.).

EXAMPLE 2

Preparation of
3-chloro-6-isopropyl-4-methyl-1,2,4-triazin-5(4H)-one hydrochloride 18.6 g (0.1 mole) of 6-isopropyl-3-mercapto-4-methyl-1,2,4-triazin-5(4H)-one are suspended in 100 ml of ethyl acetate. Then 10.9 g (0.11 mole) of phosgene are introduced at room temperature. The ensuing reaction is slightly exothermic. As the reaction is not yet complete, the mixture is stirred for 1 hour at 45° C. The mixture, which is still in the form of a white suspension, is then filtered. The residue is washed with absolute diethyl ether and the resultant white powder is dried in vacuo without heating, affording 20.3 g (90.8% of theory) of 3-chloro-6-isopropyl-4-methyl-1,2,4-triazin-5(4H)-one hydrochloride with a melting point of 144° C. (dec.). The compound sublimes when heated to 45° C. in a high vacuum, yielding the free chloride with a melting point of 129° C. (dec.).

The following compounds of formula III, listed in Table 1 together with the compound of Example 1, can also be prepared in analogous manner.

TABLE 1

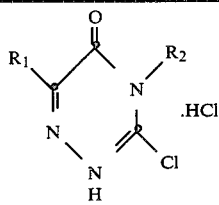

| Compound | R₁ | R₂ | Physical data |
|---|---|---|---|
| 1.1 | isoC₃H₇ | CH₃ | m.p. 144° C. (dec) |
| 1.2 | cyclohexenyl | CH₃ | m.p. 154–155° C. |
| 1.3 | cyclohexenyl | C₂H₅ | m.p. 134–135° C. |
| 1.4 | tert-C₄H₉ | CH₃ | m.p. 160° C. (dec) |
| 1.5 | cyclohexenyl | CH₃ | m.p. 118° C. (dec) |
| 1.6 | sec-C₄H₉ | CH₃ | m.p. 121° C. (dec) |
| 1.7 | CH(C₂H₅)₂ | CH₃ | m.p. 112° C. (dec) |
| 1.8 | CH₃ | CH₃ | m.p. 165° C. (dec) |
| 1.9 | tert-C₄H₉ | C₂H₅ | m.p. 148° C. (dec) |
| 1.10 | C₂H₅ | CH₃ | |
| 1.11 | C₂H₅ | C₂H₅ | |
| 1.12 | n-C₃H₇ | CH₃ | |
| 1.13 | iso-C₃H₇ | C₂H₅ | |
| 1.14 | CH₃ | C₂H₅ | |
| 1.15 | CH₃ | n-C₃H₇ | |
| 1.16 | CH₃ | iso-C₃₇ | |
| 1.17 | CH₃ | n-C₄H₉ | |
| 1.18 | 4-Cl-cyclohexenyl | CH₃ | |
| 1.19 | 4-CH₃-cyclohexenyl | CH₃ | |
| 1.20 | 2-Cl-cyclohexenyl | CH₃ | |
| 1.21 | 2-CH₃-cyclohexenyl | CH₃ | |
| 1.22 | 4-CF₃-cyclohexenyl | CH₃ | |
| 1.23 | 2-CF₃-cyclohexenyl | CH₃ | |

TABLE 1-continued

[Structure: R₁-C(=O)-C(=N-NH-)-N(R₂)-C(Cl)= ring, ·HCl]

| Compound | R₁ | R₂ | Physical data |
|---|---|---|---|
| 1.24 | CH₂-C₆H₅ (benzyl) | CH₃ | |
| 1.25 | CH₂-C₆H₄-Cl | CH₃ | |
| 1.26 | CH₂-C₆H₄-OCH₃ | CH₃ | |
| 1.27 | C₆H₄-OCH₃ | CH₃ | |
| 1.28 | C₆H₃(Cl)(Cl) | CH₃ | |

EXAMPLE 3

Preparation of 3-dimethylamino-6-isopropyl-4-methyl-1,2,4-triazin-(54H)-one 30.0 g (0.15 mole) of 3-chloro-6-isopropyl-4-methyl-1,2,4-triazin-5(4H)-one hydrochloride are suspended in 60 ml of toluene. With gentle cooling, a solution of 20.4 g (0.45 mole) of dimethylamine in 80 ml of toluene is run into the above still just stirrable mixture at about 30° C. over 2 minutes. The cooling is removed and the reaction mixture exotherms to 50° C. The reaction is complete after stirring for 15 minutes. The mixture is thoroughly stirred in 50 ml of cold water and the organic phase is separated, dried over magnesium sulfate and evaporated to dryness, affording a pale beige-coloured, clear oil in quantitative yield. Distillation yields 21.4 g (72.8%) of 3-dimethylamino-6-isopropyl-4-methyl-1,2,4-triazin-5(4H)-one as a clear, colourless oil with b.p. 135° C./0.04 mm.

The following compounds listed in Tables 2 and 3, together with the compound of this Example, can also be prepared in analogous manner.

TABLE 2

(novel compounds)

[Structure: R₁-C(=O)-C(=N-N=)-N(R₂)-C(=)-N(R₃)(R₄) triazine ring]

| Compound | R₁ | R₂ | R₃ | R₄ | Physical data |
|---|---|---|---|---|---|
| 2.1 | cyclohexyl | CH₃ | H | CH₃ | m.p. 160–161° C. |
| 2.2 | tert-C₄C₉ | CH₃ | H | CH₃ | m.p. 197–198° C. |
| 2.3 | isoC₃H₇ | CH₃ | CH₃ | CH₃ | $n_D^{20}$ = 1.5362 |
| 2.4 | cyclohexyl | CH₃ | H | C₂H₅ | m.p. 165–167° C. |
| 2.5 | CH(C₂H₅)₂ | CH₃ | H | CH₃ | m.p. 125–126° C. |
| 2.6 | sec-C₄H₉ | CH₃ | H | CH₃ | m.p. 129–130° C. |

TABLE 3

(known compounds)

[Structure: R₁-C(=O)-C(=N-N=)-N(R₂)-C(=)-N(R₃)(R₄) triazine ring]

| Compound | R₁ | R₂ | R₃ | R₄ | Physical data |
|---|---|---|---|---|---|
| 3.1 | isoC₃H₇ | CH₃ | H | CH₃ | m.p. 109–110° C. |
| 3.2 | C₂H₅ | CH₃ | piperidino | | m.p. 132° C. |
| 3.3 | tert-C₄H₉ | CH₃ | CH₃ | CH₃ | m.p. 87–88° C. |
| 3.4 | cyclohexyl | CH₃ | CH₃ | CH₃ | m.p. 104–106° C. |
| 3.5 | sec-C₄H₉ | CH₃ | CH₃ | CH₃ | $n_D^{20}$ = 1.5325 |
| 3.6 | CH(C₂H₅)₂ | CH₃ | CH₃ | CH₃ | |
| 3.7 | 1-methyl-cyclobutyl | CH₃ | CH₃ | CH₃ | |
| 3.8 | cycloheptyl | CH₃ | CH₃ | CH₃ | |
| 3.9 | phenyl | CH₃ | H | CH₃ | m.p. 227–229° C. |
| 3.10 | phenyl | CH₃ | H | H | m.p. 270° C. |
| 3.11 | phenyl | CH₃ | morpholino | | m.p. 130° C. |
| 3.12 | phenyl | CH₃ | n-C₄H₉ | n-C₄H₉ | m.p. 135–145° C. |
| 3.13 | phenyl | CH₃ | CH₃ | CH₃ | m.p. 111–112° C. |

FORMULATION EXAMPLES

Formulation Examples for liquid active ingredients of the formula I (throughout, percentages are by weight)

| 4. Emulsifiable concentrates | (a) | (b) | (c) |
|---|---|---|---|
| a compound of table 2 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 5. Solutions | (a) | (b) | (c) | (d) |
|---|---|---|---|---|
| a compound of table 2 | 80% | 10% | 5% | 95% |

-continued

| 5. Solutions | (a) | (b) | (c) | (d) |
|---|---|---|---|---|
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| 6. Granulates | (a) | (b) |
|---|---|---|
| a compound of table 2 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 7. Dusts | (a) | (b) |
|---|---|---|
| a compound of table 2 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples for solid active ingredients of the formula I (throughout, percentages are by weight)

| 8. Wettable powders | (a) | (b) | (c) |
|---|---|---|---|
| a compound of table 2 | 25% | 50% | 75% |
| sodium lignosulfonate | 5% | 5% | — |
| sodium lauryl sulfate | 3% | — | 5% |
| sodium diisopropylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| 9. Emulsifiable concentrate | |
|---|---|
| a compound of table 2 | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 10. Dusts | (a) | (b) |
|---|---|---|
| a compound of table 2 | 5% | 8% |
| talcum | 95% | — |
| kaolin | — | 92% |

Ready-for-use dusts are obtained by mixing the active ingredient with the carriers, and grinding the mixture in a suitable mill.

| 11. Extruder granulate | |
|---|---|
| a compound of table 2 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a strem of air.

| 12. Coated granulate | |
|---|---|
| a compound of table 2 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 13. Suspension concentrate | |
|---|---|
| a compound of table 2 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

EXAMPLE 14

Preemergence herbicidal activity

In a greenhouse, immediately after sowing the test plants in pots of 11 cm diameter, the surface of the soil is treated with an aqueous emulsion of the test compound at a concentration corresponding to 4 kg of active ingredient per hectare. The pots containing the seeds are kept in the greenhouse at 20° to 24° C. and 50 to 70% relative humidity. The test is evaluated after 3 weeks and the results are assessed in accordance with the following rating:

| | | |
|---|---|---|
| 1 | = | plants have not germinated or are completely withered |
| 2–3 | = | very pronounced activity |
| 4–6 | = | average activity |
| 7–8 | = | slight activity |
| 9 | = | no activity (as untreated controls). |

The results are reported in the following table.

TABLE 4

| Compound | Preemergence activity | | | |
|---|---|---|---|---|
| | Avena | Setaria | Sinapis | Stellaria |
| 2.1 | 3 | 2 | 1 | 2 |
| 2.2 | 1 | 1 | 1 | 1 |
| 2.3 | 1 | 1 | 1 | 1 |
| 2.4 | 1 | 1 | 1 | 1 |
| 2.5 | 1 | 1 | 1 | 1 |
| 2.6 | 1 | 1 | 1 | 1 |

EXAMPLE 15

Postemergence herbicidal activity

In a greenhouse, the following plants are grown in pots of 11 cm diameter until they have reached the 3-leaf stage (about 2 weeks): soybeans, *Avena fatua*, Setaria, Lolium, Solanum, Stellaria, Sinapis and Phaseolus. The plants are then sprayed with an aqueous emulsion of test compound at a concentration corresponding to 4 kg of active ingredient per hectare, and then kept at 20°–24° C. and 45–60% relative humidity. Evaluation of the test is made after 15 days and the results are expressed in accordance with the same rating as employed for the preemergence test. The results are as follows:

TABLE 5

| Compound | Postemergence activity | | | | | | |
|---|---|---|---|---|---|---|---|
| | Avena | Setaria | Lolium | Solanum | Sinapis | Stellaria | Phaseolus |
| 2.1 | 1 | 1 | 2 | 1 | 1 | 1 | 3 |
| 2.2 | 1 | 1 | 1 | 1 | 1 | 1 | 3 |
| 2.3 | 1 | 1 | 1 | 1 | 1 | 1 | 2 |
| 2.4 | 1 | 2 | 1 | 1 | 1 | 2 | 4 |
| 2.5 | 1 | 1 | 1 | 1 | 1 | 1 | 2 |
| 2.6 | 1 | 1 | 1 | 1 | 1 | 1 | 2 |

What is claimed is:

1. A 3-chlorotriazinone derivative of the formula

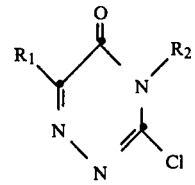

wherein $R_1$ and $R_2$, each independently of the other, are $C_1$–$C_8$-alkyl which is unsubstituted or substituted by $C_1$–$C_4$-alkoxy or halogen; $C_3$–$C_8$-cycloalkyl which is unsubstituted or substituted by methyl; benzyl which is unsubstituted or substituted by one or more members selected from the group consisting of halogen, $C_1$–$C_8$-alkyl, $C_1$–$C_4$-haloalkyl and $C_1$–$C_4$-alkoxy; or are phenyl or naphthyl which is unsubstituted or substituted by one or more members selected from the group consisting of $C_1$–$C_8$-alkyl, halogen, $C_1$–$C_4$-haloalkyl and $C_1$–$C_4$-alkoxy, or a hydrochloride thereof.

2. A 3-chlorotriazinone derivative of claim 1, wherein $R_1$ is unsubstituted $C_1$–$C_5$-alkyl or cyclohexyl and $R_2$ is methyl.

3. A 3-chlorotriazinone derivative of claim 1 selected from the group consisting of 6-(1-ethyl-n-propyl)-4-methyl-3-chloro-1,2,4-triazin-5(4H)-one, 6-sec-butyl-4-methyl-3-chloro-1,2,4-triazin-5(4H)-one, 6-cyclohexyl-4-methyl-3-chloro-1,2,4-triazin-5(4H)-one, 6-tert-butyl-4-methyl-3-chloro-1,2,4-triazin-5(4H)-one and, 6-isopropyl-4-methyl-3-chloro-1,2,4-triazin-5(4H)-one.

* * * * *